United States Patent [19]  [11] 4,127,447
Griffith et al.  [45] Nov. 28, 1978

[54] BIOMASS GROWTH RESTRICTION IN A PACKED BED REACTOR

[75] Inventors: William L. Griffith, Oak Ridge; Alicia L. Compere, Knoxville, both of Tenn.

[73] Assignee: The United States of America as represented by the United States Department of Energy, Washington, D.C.

[21] Appl. No.: 682,801

[22] Filed: May 3, 1976

[51] Int. Cl.$^2$ .................... C12B 1/00; C12C 11/08; C02C 1/14
[52] U.S. Cl. ............................. 195/116; 195/2; 195/32; 195/57; 195/59; 195/DIG. 11; 195/117; 210/2
[58] Field of Search .............. 195/59, 27, 31, 2, 115, 195/116, 117, 110, 111; 210/2, 11, 17

[56] References Cited

U.S. PATENT DOCUMENTS

| | | | |
|---|---|---|---|
| 3,402,103 | 9/1968 | Amberg et al. | 195/116 X |
| 3,580,840 | 5/1971 | Uridil | 210/11 |
| 3,711,392 | 1/1973 | Metzger | 210/11 X |
| 3,886,046 | 5/1975 | Young et al. | 195/115 |
| 3,935,067 | 1/1976 | Thayer | 195/116 X |
| 4,005,010 | 1/1977 | Lunt | 210/17 |
| 4,009,286 | 2/1977 | Moll et al. | 195/116 X |

OTHER PUBLICATIONS

Enzymes Technology, C & EN, 1975 (pp. 22-32).
Lawrence, et al., Unified Basis for Biological Treatment Design and Operation, Journal of the Sanitary Engineering Division, Jun. 1970, (pp. 757-778).
Swenson, et al., Evidence Relating Cessation of Respiration, Cell Envelope Changes and Death in Ultraviolet-Irradiated *Escherichia coli* B/r Cells, J. of Bact. vol. 117, No. 2, 1974 (pp. 551-559).
Schenley, et al., Centrifugal Separation of Irradiated Cultures of *Escherichia coli* Cells into Viable and Nonviable Populations, J. of Bact., vol. 126, No. 2, 1976 (pp. 977-984).

*Primary Examiner*—David M. Naff
*Attorney, Agent, or Firm*—Dean E. Carlson; Stephen D. Hamel; John B. Hardaway

[57] ABSTRACT

When carrying out continuous biologically catalyzed reactions with anaerobic microorganisms attached to a support in an upflow packed bed column, growth of the microorganisms is restricted to prevent the microorganisms from plugging the column by limiting the availability of an essential nutrient and/or by the presence of predatory protozoa which consume the anaerobic microorganisms. A membrane disruptive detergent may be provided in the column to lyse dead microorganisms to make them available as nutrients for live microorganisms.

14 Claims, 6 Drawing Figures

BIOMASS GROWTH RESTRICTION IN A PACKED BED REACTOR

BACKGROUND OF THE INVENTION

This invention was made in the course of, or under, a contract with the Energy Research and Development Administration. It relates generally to the art of biologically catalyzed reactor systems and more particularly to a process for limiting the growth of biomass.

The advantages of continuously carrying out chemical reactions are well recognized in the field of chemical engineering and in the chemical manufacturing industries. It is well known that much savings in time and equipment can be achieved by driving a chemical reaction or separation to completion under steady state conditions as opposed to operating a series of batch reactors. In certain instances, however, continuous operation is difficult to attain as a result of physical and mechanical problems. Biologically catalyzed reactions such as fermentation, biodegradation and biochemical transformations such as racemization are reaction types wherein such problems lie.

Biologically catalyzed reactions have previously been carried out in stirred tank reactors and in packed bed reactors on a near continuous basis. Stirred tank biological reactors operate in a mode such that excess biomass is accommodated. Excess biomass in this reactor type is removed along with the effluent flow and partially recycled to the reactor. Packed bed reactors, however, have no provision for handling excess biomass. If the flow of reactants is suitably rapid, excess biomass will be swept from the column. If the flow rate is reduced, biomass will sediment within the reactor, resulting in low surface area and low specific activity. If the flow rate is reduced as suggested above, or if filtration is imposed to prevent carry-out of the biomass by the effluent liquid, the volume of biomass increases causing pressure differentials and reduction in biological activity. Periodic removal of biomass in part or complete repacking of the reactor may be required in order to continue the process.

SUMMARY OF THE INVENTION

It is thus an object of this invention to provide a process for continuously carrying out biologically catalyzed reactions.

It is a further object of this invention to provide a continuous process wherein biomass growth is restricted.

These as well as other objects are accomplished by introducing an influent of reactants into the bottom of an upflow column having anaerobic microorganisms attached to a support therein for catalyzing the reaction while simultaneously limiting the population of the microorganisms.

DETAILED DESCRIPTION OF THE DRAWINGS

In accordance with this invention it has been found that continuous biologically catalyzed anaerobic processes may be conducted in a manner so as to alleviate the problems which exist in the prior art batch processes as well as overcoming problems which inhere in the use of continuous fixed film packed bed upflow reactors. By use of a continuous system the reculturing of appropriate biological catalysts for each batch is not required. The avoidance of reculturing is particularly advantageous when the catalyst used is an anaerobic bacteria because such cultures are well known to be difficult to grow.

Figure 1:
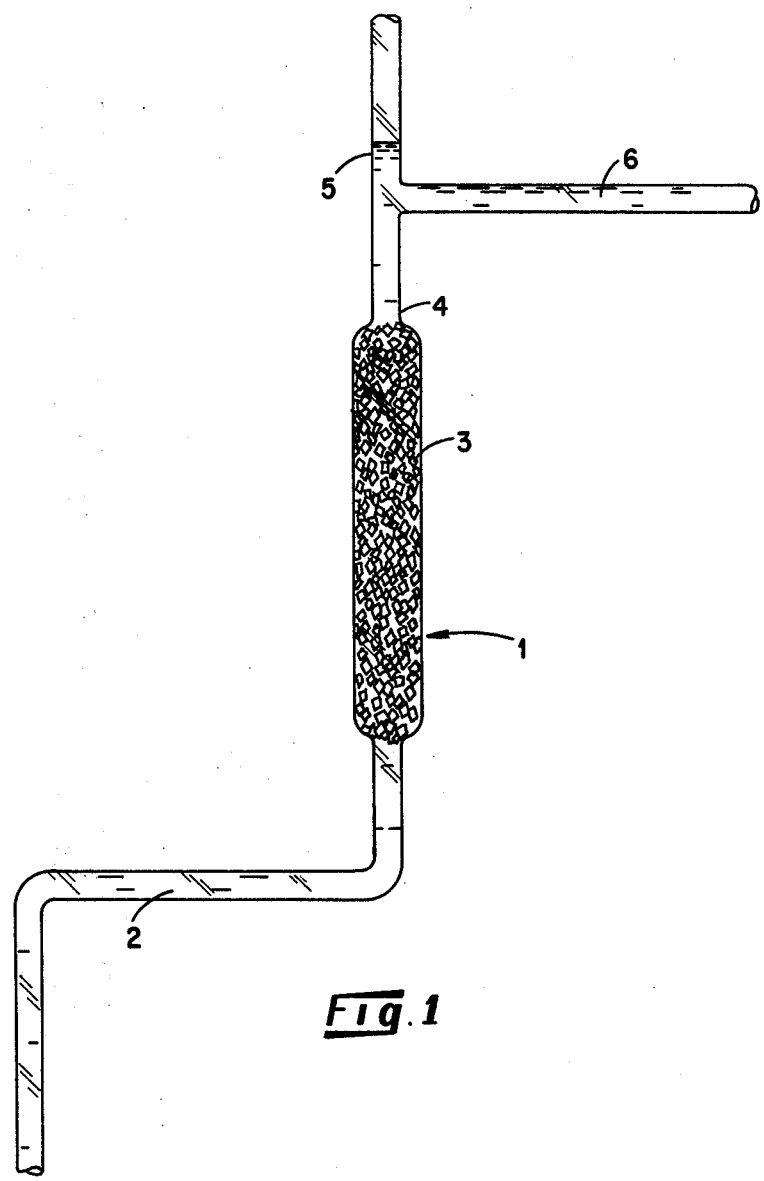
FIG. 1 schematically depicts an apparatus for use in the process of this invention.
Figure 2:
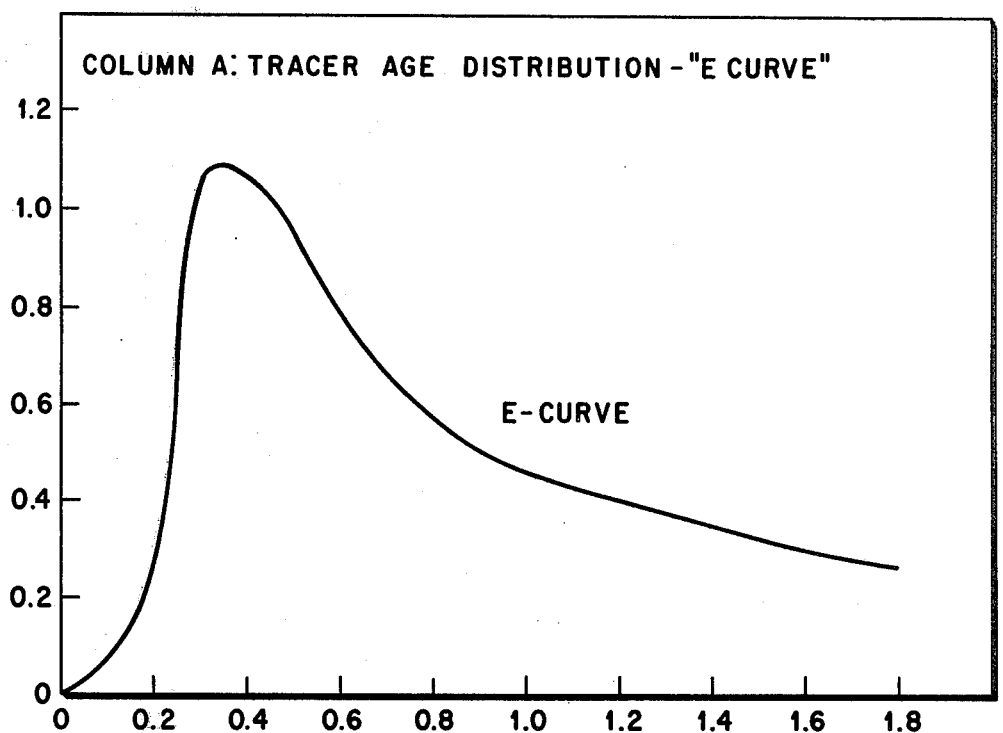
FIGS. 2 through 6 graphically illustrate data obtained from operation of the process of this invention.
Figure 3:
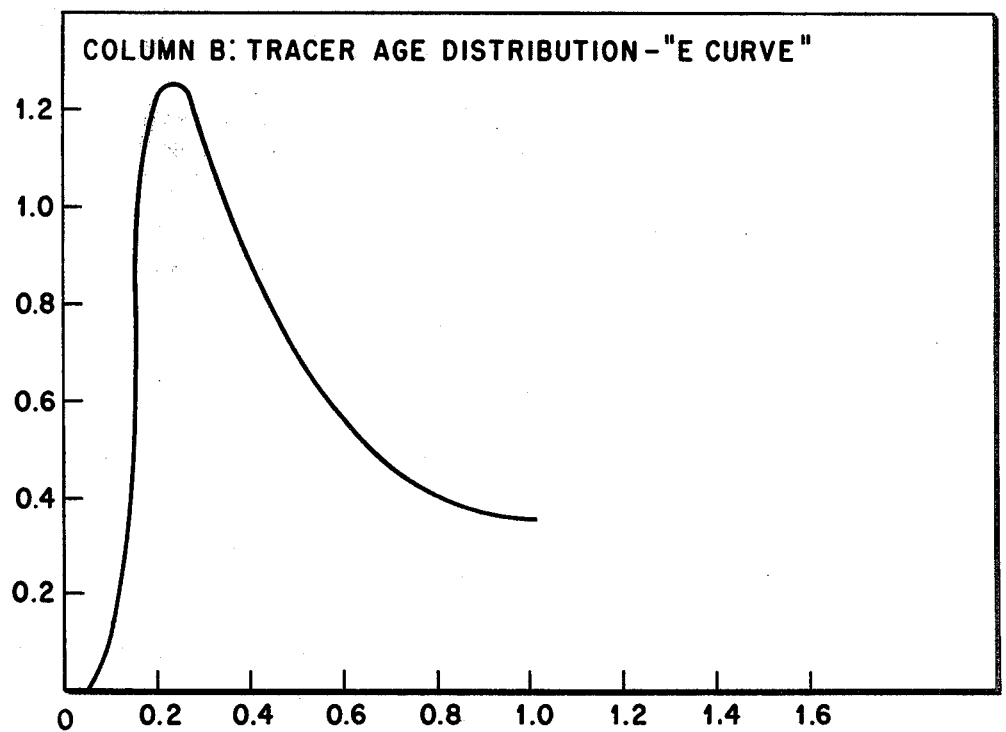
Figure 4:
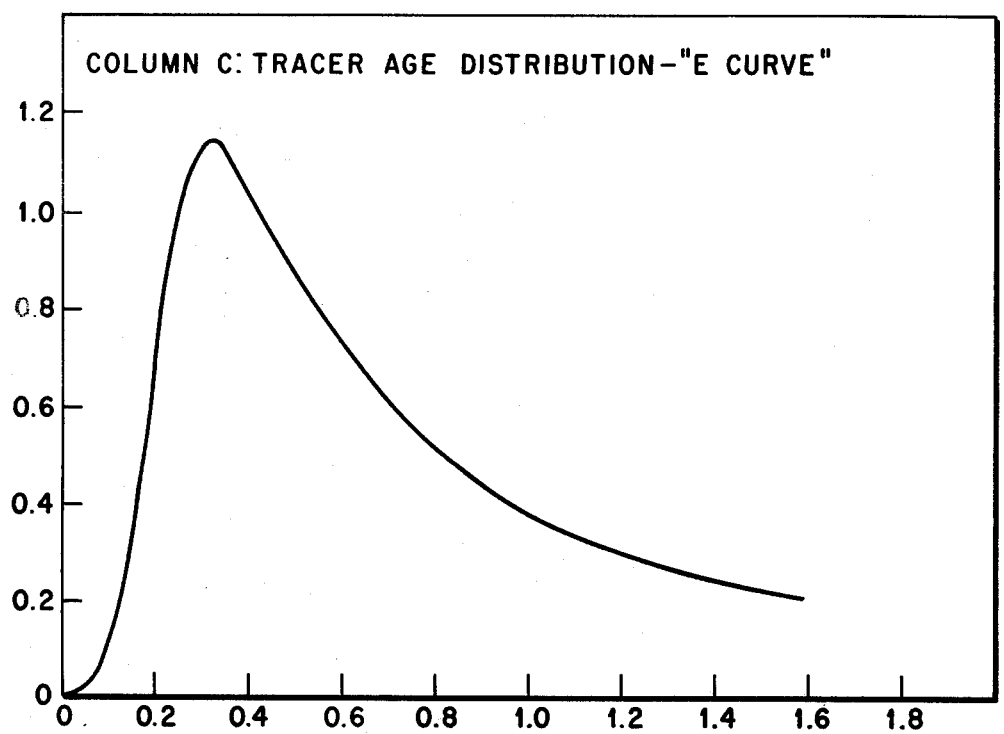
Figure 5:
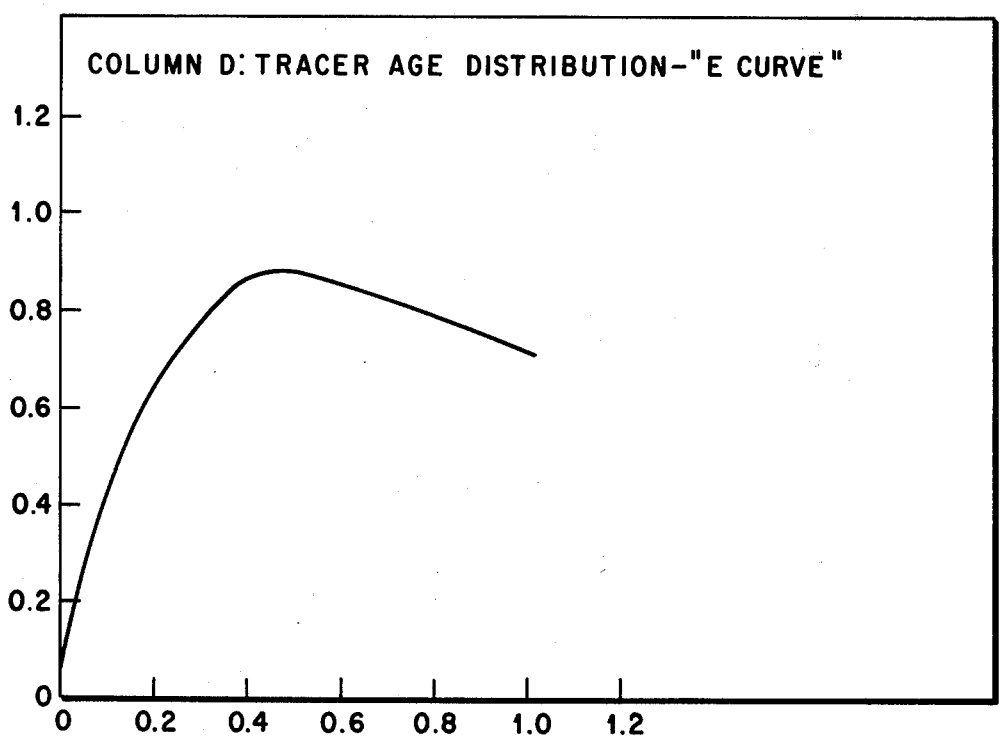

The process and embodiments within the scope of this invention may be best understood by first referring to the apparatus in which the process of this invention is carried out. Such apparatus is shown in FIG. 1 of the drawings. The apparatus comprises a packed column 1 having a source of influent or reactants 2. The column is packed with a support 3 to which the biological catalysts are attached. The products of the reaction leave the columns via exit 4 such that any gaseous products may be vented or extracted through outlet 5 while liquid products are removed through exit 6. This type of reactor unit is referred to in this disclosure as an anaerobic upflow packed bed bioreactor. As used within this disclosure, the term anflow process refers to chemical reactions conducted in such an apparatus. The term itself is an acronym for anaerobic upflow.

An essential part of the apparatus used in carrying out an anflow process is the packing material 3 to which the anaerobes are attached. The packing material may be a conventional material used in distillation tower packings, such as alumina, porcelain, stoneware, or fired clays, or less conventional materials, such as mixed cement compositions. Such packing material may be coated by the technique described in commonly assigned copending application Ser. No. 701,479 filed June 30, 1976 of common inventorship. Such technique involves coating a dense packing material with a polymer which can be cross-linked to form an insoluble hydrophilic loose net film to which microorganisms are attached. The packing can thus be a dense material such as glass, stone, ceramic or plastic which is coated with a hydrogel form material such as gelatin, egg albumin, hide pulp collagen, refined collagen, fibrin, fluten and acrylic acid backbone type polyelectrolytes such as polycrylamide and polyhydroxy-ethyl methacrylate. Such polymer can then be cross-linked with an agent selected from the group consisting of gluteraldehyde, ethylchloroformate, formaldehyde, dimethyl adepimidate, N,N'-methylenebisacrylamide, 1,2-diacrylamide ethyleneglycol, and N,N'-diallyltartardiamide. The anaerobic microorganisms can be attached either before or after cross-linking. Other types of packings which may be used in the anflow apparatus include those which are capable of forming a hydrophilic charged layer on their surface as a function of their composition. Such materials include various charged metals and metal oxides or hydroxides, and substituted plastics, such as ion-exchange resins.

When the process of this invention is not employed, the anaerobic organisms which are attached to the packing in the above manner when contacted with the reactant solutions which are to be metabolized tend to expand and grow such that the actual volume of anaerobes (biomass within the column) becomes considerably greater after a short period of operation. This expanded volume of biomass tends to plug the column making further operation impossible. This biomass includes both organisms which are alive and active as well as anaerobes which have died and are no longer contributing to the utility of the process. The essence of this invention is the discovery that the volume of biomass can be restricted by limiting the population of anaerobes within the column while simultaneously allowing the anaerobes to catalyze the particular reaction via their metabolic activity.

One aspect of the process of this invention comprises restricting an essential growth nutrient. Microorganisms need various nutrients in order to perform their function within the column. Some of these nutrients are the reactants which are metabolized by the microorganisms during the course of chemical reaction. Other nutrients are needed by the organisms in order to carry out their metabolic function. Such nutrients include metallic ions which are necessary for use in coenzymes and in the prosthetic groups of some proteins, various vitamins and cofactors which are required by the organism but are not manufactured from the feedstock by the organism, and the necessary constituents of cell enzymes which are not made from the fermentation feedstock by the organisms.

Other nutrients utilized by microorganisms are known as essential nutrients for growth. Thus, in accordance with this invention, it has been found that by restricting and even eliminating the nutrients which are essential for growth the population of microorganisms within the column can be maintained constant. This is quite surprising in view of the expectation that the microorganisms would slowly die off and decrease in population as a result of the non-availability of essential nutrients. However, in most systems, it has been found that the microorganisms which die become a source of essential nutrients for the remaining microorganisms. By having the active microorganisms utilize the essential nutrients contained in the inactive or dead microorganisms, an equilibrium is established which limits the microorganisms population to a stable size. In some instances, the essential nutrient may be entirely eliminated from an influent solution and a stable population will be maintained. In other systems a trace of the nutrient must be present to maintain a stable population. For example, the growth of yeast in the presence of excess fermentable carbohydrate can be limited by the amount of nitrogen containing organic compounds and ammonia which is present in the fermentation broth. To limit yeast growth organic nitrogen containing compounds, such as urea, or inorganic nitrogen containing compounds, such as ammonia, can be restricted to the fermentation broth.

In some systems, however, it has been found that the microorganisms do not readily assimilate the biomass of the dead microorganisms into their own metabolism. However, further in accordance with this invention, it has been found that the addition of a small amount, i.e., 0.001 to 5 weight percent of a membrane disruptive detergent to the influent stream will make the nutrients of the dead microorganisms available to the live microorganisms so as to maintain a balance between the death rate and the repopulation due to microorganism population expansion. The net result is that the population remains substantially constant. As an added advantage the membrane disruptive detergent lyses inactive microorganisms from the support which allows accommodation for replacement by active organisms. As used within this disclosure, the term "membrane disruptive detergent" means a detergent which ruptures, dissolves, or other wise causes to break the membranes which enclose the whole cell mass, or other vital constituents of the cell, such as the cell nucleus. This composition includes the following types of surfactants: ionic surfactants, including those of the anionic, cationic, and generally neutral charges; non-ionic surfactants; alkyl benzene sulfonates; and other common detergents and surfactants. In some cases, specific membrane cleaving enzymes, such as lipases and lysozymes, or the organisms which produce them, can be employed for a like purpose.

Further techniques embodied within the scope of this invention by which the population of anaerobes is limited is by the presence within the column of predatory protozoa which consume the anaerobes performing the primary metabolic function. By simultaneously culturing microbes for use as a biological catalyst along with a predatory protazoa, a symbiotic relationship is established between the anaerobic microorganisms. By such technique the protozoa consume excess microorganisms and in so doing excrete the essential nutrients which they absorb from the consumed organisms. The essential nutrients which are excreted are consumed by the organisms performing the primary metabolic function to provide for regrowth. Such an arrangement leads to stabilization of microorganism population. This aspect of the invention may be practiced along with a restriction on essential nutrients or without restriction on essential nutrients. If nutrients are restricted the excretion products of the protozoa will provide sufficient nutrients to maintain a stable primary metabolic microorganism population. If the essential nutrients are not limited the tendency for the microorganisms performing the primary metabolic function to increase in population will be opposed by the additional consumption and growth of the protozoan population. By this mechanism the population of primary microbes remains substantially constant.

In accordance with this embodiment of the invention a unique anaerobic protozoan strain has been cultured for use in conjunction with mixed anaerobic bacteria for treating waste effluents containing dissolved organic carbon in the form of biological oxygen demand (BOD). This unique strain of protozoan was developed by culturing a mixture of rumen fluid, sewage sludge, trickling filter scrapings, dirt, sorptive charcoal particles and a conventional flocculant at ambient domestic sewage temperatures for several weeks in a packed upflow column. This is more specifically described in Example II. A mixed culture of the anaerobic bacteria along with the cultured anaerobic protozoan of this invention is contained in the American Type Culture Collection, 12301 Parklawn Drive, Rockville, Md. and given ATCC No. 30539 on Apr. 27, 1976. This symbiotic combination of anaerobic microorganisms is preferably attached to a stoneware or porcelain support so as to be utilized in an anflow column such as that shown in the figure of drawing. By utilizing such an arrangement the organic carbon or BOD of either industrial or sanitary sewage effluents is converted to methane as follows:

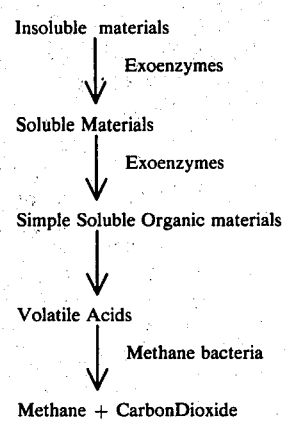

At present, the treatment of sewage effluents by this anaerobic technique represents a 75% savings in capital investment as well as a 75% decrease in the power consumption of the digestion process as compared to a conventional aerobic process. Such a process also has an unexpected advantage in that the reaction rate from the use of an anflow unit is about five times greater per unit volume than a comparable aerobic unit.

The anflow unit utilizing the mixed culture of this invention can be used to treat pulp and papermill wastes, tannery wastes, other industrial organic wastes as well as domestic sewage. Although waste mixtures can be treated in the range of pH values between 3 and about 10, the optimum range depends upon the culture and the waste materials processed. It is essential to avoid contacting the microorganisms with materials which might kill them. Such materials include those with high redox potentials, those which have known bactericidal properties, including polyaromatics, polyphenolics, bacteriostatics, chlorine and other halogenic materials, pesticides, and cyanide.

Having generally described the process of this invention the following specific examples are given as a further illustration thereof.

EXAMPLE I

A column similar to the column shown in the figure of drawing was used to convert glucose to ethanol. The column was 1.5 inches in inside diameter and 24 inches long. The column was constructed of glass and packed with ¼ inch berl saddles and ¼ inch glass beads. A coating for the packing was produced by forming a mixture of:

25 ml of 1 gram/liter polyelectrolyte solution (A-23 by Dow)
  10 ml formaldehyde solution
  5 ml formamide solution
  5 grams gelatin dissolved in 20 ml water previous to addition.

This was stirred with 1 quart of packing material in a rotary tumbler until there was no formaldehyde odor. The resulting packing was dried and baked at 60 to 80° C. for 6 to 8 hours. Yeast cream was prepared as follows:

To 5 grams of active dry ethanol tolerant yeast culture was added
  10 ml water
  10 ml of a 1 gram per liter solution of Calgon polyelectrolyte CP #8, 3.1 Milliequivalent/gram
  20 ml saturated ferric chloride solution.

This was mixed vigorously between additions and passed through a Dounce homogenizer using a loose pestle. The mixture was centrifuged and the pellet resuspended in:

1 ml saturated sodium propionate
  1 gram alum
  1 gram magnesium sulfate heptahydrate
  10 ml of a 1 gram per liter solution of Calgon CP #8
  20 ml water.

This was again centrifuged and the pellet resuspended in a small amount of water to form a cream. The yeast cream and the coated packing were then placed in a rotary tumbler and tumbled until a good coating was formed. Bottom yeast cultures were mixed with a 1% solution of Nalco 8172 polyelectrolytes prior to being introduced into a sterilized aqueous feed solution consisting of 1% yeast extract and 5 to 30 weight percent glucose and was passed upwardly through the column at about 900 ml per day. During a 1 month start-up period, to optimize yeast multiplication and to enhance attachment to the coated packing, aqueous feed solution containing 1% yeast extract and sufficient malt extract to give a specific gravity of 1.02 was passed through the column at about 900 ml per day. Following the start-up period "Difco" yeast extract, the water soluble portion of autolyzed yeast, which was the source of metabolizable nitrogen (an essential growth nutrient) was reduced by a factor of 5 to 0.2% to restrict the growth of the biomass population.

The packed column now having a yeast culture well established on the coated packing was operated continuously on an experimental production basis for 26 weeks. Feed solutions ranging from 20 to 30% glucose were passed upward through the column at several flow rates. The operating characteristics of this yeast column are given in Table I below.

TABLE I

| OPERATING CHARACTERISTICS OF YEAST COLUMN | | | | | |
|---|---|---|---|---|---|
| In | Out | Used | Ethanol (%) | Flow (ml/day) | Detention Time (hours) |
| 20 |  | 20 | 11 | 900 | 8.8 |
|  |  |  |  | 950 | 8.3 |
|  |  |  |  | 1400 | 5.7 |
|  |  |  |  | 1450 | 5.5 |
|  |  |  |  | 1500 | 5.3 |
| 26 | 0.2 | 25.8 | 15 | 750 | 10.6 |
|  |  |  |  | 1300 | 6.1 |
|  |  |  |  | 3550 | 2.2 |
| 30 | 12 | 18 | 10 | 1200 | 6.6 |
|  | 2.5 | 27.5 | 15.5 | 1430 | 5.5 |

The process was stable to variations in feed glucose concentrations between 5 and 30 percent by weight. During processing, pH values were tested between pH 3 and pH 8. However, very little effect upon alcohol performance was noted within that range. During this period, the source of metabolizable nitrogen was yeast extract (Difco). This material was maintained at a concentration of one weight percent. The unit operated stably for a period of several months which is significantly longer than the culture use (1 to 2 weeks) in commercial stirred reactors.

EXAMPLE II

A culture composed of both bacteria and several bacterial population consumers, including protozoans and other invertebrates was prepared from 4 gallons of whole rumen fluid and 10 gallons of sewage sludge mixed with 25 grams of Calgon polyelectrolyte CP #8 and 20 grams of alum. The mixture was blenderized in aliquots and sieved. It was then composited and pumped into the base of a set of five columns. The columns had been filled previously with several different types of stoneware and chemical porcelain packing soaked in a saturated ferric chloride solution followed by charcoal dust and gelatin solution by passing the solutions through the dry packing several times until the compounds were absorbed and the packing appeared colored. The excess solution was then drained from the units, and the blenderized mixture added. The units were started by passing sewage slowly through them from the bottom to the top, using a small Cole-Parmer peristaltic pump. After a period of time, observations indicated that there was a vigorous population of microorganisms growing in the columns. There were also several different types of microscopic protozoans. These were generally anaerobic flaggelates and cilliates. Most of the species observed were similar to those which are found in rumen fluid, indicating that they had survived the seeding process. Free living nemotodes are also present. A culture of this mixture is filed as above referenced with the American Type Culture Collection.

EXAMPLE III

An experiment utilizing the columns of Example II with a municipal sewage influent was designed as a factorial experiment employing the possible combinations of two void fractions and two relative amounts of surface area per unit packing volume. An empty column of identical design was operated concurrently with the other units in order to provide a wall effect and sedimentation control. The combinations of void fraction and packing surface area are shown in Table II.

Table II

| Column | Parameter | | | |
|---|---|---|---|---|
| | Packing Surface Area | Void Fraction | Type | Material |
| A | 119 | 0.36 | Pellet | Stoneware |
| B | 102 | 0.71 | Intalux | Ceramic |
| C | 39 | 0.41 | Pellet | Stoneware |
| D | 32 | 0.75 | Berl Sad. | Stoneware |
| E | | 1.00 | Empty | |

The units used were plexiglass cylinders 6 feet in height by 8 inches in diameter fitted with phase separators at the top and sample taps at 6 inch intervals along the length. The units had a bed limiter which provided some flow distribution at the bottom. The flow distributors were made of nylon, which provided both a relatively non-fouling support together with some flow distribution.

Upon installation, the units were levelled to prevent channelling due to passage of gas bubbles along the upper side and solids along the lower side. The column units were constructed of extruded tubing, with the cylindrical sections relatively free from defects which might cause eddies in the flow during operation at the planned flowrates.

The units were started in the manner described in Example II. The packing was placed in the units, and was weighed and the void fractions determined. The units were then moved to a sewage plant, and were coated sequentially with ferric chloride solution, and anionic flocculant (Nalco #8172 polyelectrolyte), finely divided charcoal, and gelatin. A mixture consisting of finely divided rumen fluid, sewage sludge, and a small amount of dirt was added to the units. Sewage was then introduced into the units from the bottom, and allowed to pass upward through the mixture.

The units were fed concurrently by a peristaltic pump which provided feed for, and took samples from, all five units. This insured that each unit received the same flow of the same feed. A separate pump was used to take feed samples. All samples were stored in a refrigerator during the sampling period, so that changes in BOD were limited. Considerable care was taken to be sure that a representative aliquot was analyzed from each 24-hour continuous sample.

Samples were routinely examined for BOD, TOC, and suspended solids. The BOD samples were processed according to the method described in *Standard Methods for the Examination of Water and Wastewater*. All BOD samples were routinely replicated to avoid the errors that can arise from distribution of solid materials within the sample. Samples for TOC analysis were prepared in the same manner that the BOD samples are, but were generally ground using a Dounce homogenizer. This reduced the size of suspended particles so that good 20 to 40 microliter samples could be taken. The TOC samples were analyzed using a Beckman model 915 TOC analyzer. Suspended solids were determined using a modification of the glass crucible method which uses Whatman GF/C glass fiber filters. Total suspended solids were determined after firing at 103° C. Volatile solids are determined by difference after firing at 600° C.

Figure 6:
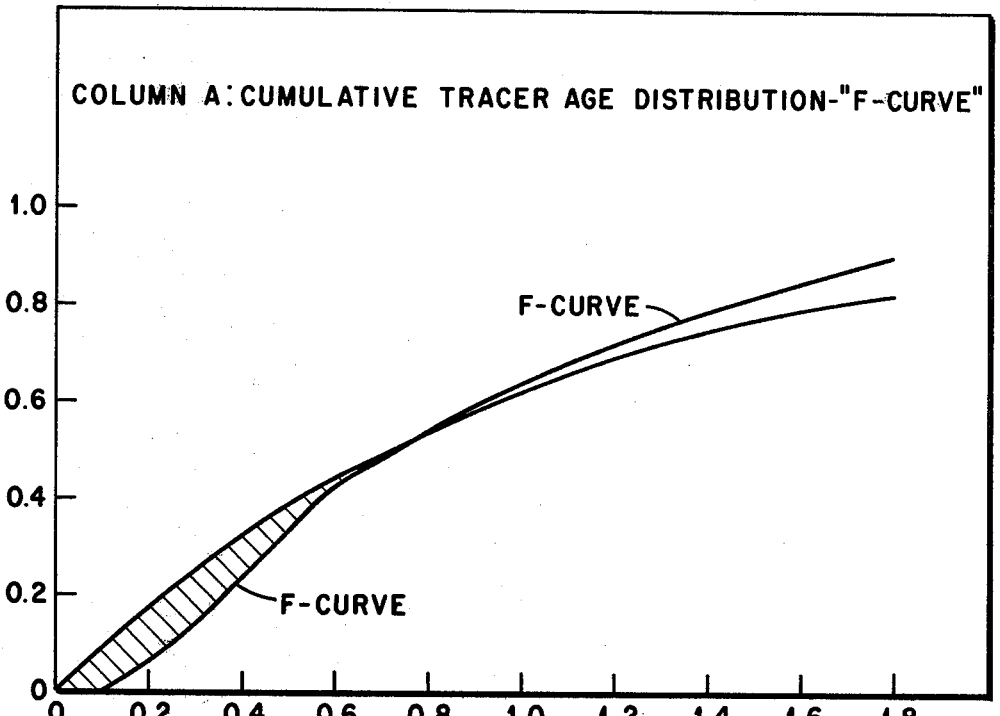

Dye tracer studies have been performed to provide information on the hydraulic characteristics of each of the units. FIGS. 2 through 5 show the E, or age distribution, curves for column A through D. FIG. 6 shows the F, or cumulative age distribution curve, for column A together with the ideal mixing curve. It is apparent from the curves plotted that there is a mixing regime in these units which is somewhere between plug flow and longitudinal mixing. The amount of segregation shown in FIG. 6 indicates that there is a deviation from complete mixing in the system.

The values obtained for the units operating at the sewage plant are shown in Table III. The units have void fractions ranging from 0.36 to 0.75, and corresponding void volumes ranging between 19.1 and 39.5 liters, based on actual measurement prior to startup. The apparent diffusion coefficients, in cm/sec, ranged from 0.2 to 0.7, with most of the values at 0.6 to 0.7. The segregation factor, S, which is a dimensionless factor measuring the difference in the mixing pattern from complete mixing, ranged between 0.028 to 0.066. The low void fraction and the high void fraction low surface area units had higher segregation factors, clumping around 0.05–0.066, than did the high surface area high void fraction unit.

Table III

| Parameter | Column | | | |
|---|---|---|---|---|
| | A | B | C | D |
| Void Volume, V, liters | 19.1 | 38.6 | 21.4 | 39.5 |
| Void Fraction | 0.36 | 0.71 | 0.41 | 0.75 |
| Apparent Diffusion Coefficient, D, cm$^2$/sec | 0.7 | 0.6 | 0.7 | 0.2 |
| Segregation Factor, S | 0.049 | 0.028 | 0.066 | 0.052 |

Two different methods of sampling were used. One of the methods used was the taking of samples at 1 foot intervals of column height. In general, the feed and effluent samples were not centrifuged prior to analysis. The samples which were taken from the center of the column were centrifuged to remove any particles of bacterial slime which might have come out with the sample. This is a standard method for preparing samples from fixed film systems. The other method used was to collect continuous column samples for a period of 24 hours. The samples were collected from the effluent lines of the column gravity legs using ⅛ inch teflon tubing. They were removed using small peristaltic heads which were attached to the column feed pump. The samples were fed from the columns through the pump into large sample bottles in the refrigerator. Matching feed samples were collected using a similar pump. However, these were taken for 3 minutes out of 15 so that a larger, faster pumping head could be used to decrease the problems of pumping the solids contained in the sewage. It was felt that the sampling from a continuously stirred barrel at frequent time intervals gave satisfactory results. The time intervals for feed sampling were at least an order of magnitude more frequent than the time required to feed a barrel of sewage through the five units.

Table IV shows a traverse through each of the five columns during operation at a flow rate of 240 ml per minute per column, as $BOD_5$. The figures are given as removal efficiency. From considering the data, two different points will become readily apparent. The first point is that there is a complex series of reactions going on in the units. In some cases, the removal efficiency actually decreases with column height. This is probably due to the degradation of insoluble polymers into soluble subunits. This also causes the units to exhibit a BOD decrease which is not a single exponential function, but rather represents a series of reactions. At this higher flow rate, it is also apparent that either surface area or the plug-flow nature of the hydraulic regime enforced by the higher surface area packing provided for more efficient BOD removal.

Table V shows the suspended solids removal by these units. The values given are the average of two replicate samples. It is clear in this case that the suspended solids removal by the two high-surface area units and by the empty column is very good, averaging over 90%. However, it appears that the other two units also provided over 80% suspended solids removal.

Table IV

| | $BOD_5$ Removal Efficiency | | | | |
|---|---|---|---|---|---|
| | Column | | | | |
| Bed Depth, ft. | A | B | C | D | E |
| 1 | 77% | 33.8% | 23.9% | 31.8% | 78.4% |
| 2 | 81.3% | 69.3% | 69.9% | 0% | 88.7% |
| 3 | 76.1% | 62.5% | 65.6% | 19.9% | 89.8% |
| 4 | 77.8% | 78.2% | 64.3% | 42.0% | 85.6% |
| 5 | 75.3% | 70.8% | 60.8% | 67.6% | 89.8% |
| 6 | 100% | 96.6% | 83.0% | 83.8% | 90.7% |

Table V

| Suspended Solids Removal Efficiency | |
|---|---|
| Unit | Removal Efficiency, % |
| A | 95.5 |
| B | 93.4 |
| C | 88.2 |
| D | 82.2 |
| E | 95.1 |

The removal of volatile suspended solids by these units was also considered. Volatile suspended solids is the amount of suspended solids which can be removed by firing the suspended solids at 600° C. To a certain extent, it is a measure of the amount of carbonaceous matter which is present in a sample. It does, however, also include any inorganic salts, such as calcium carbonate, which volatilize at this temperature. Table VI gives the removal efficiencies of volatiles suspended solids in the five units at the 240 ml/minute/unit flow rate. The higher surface area units were superior to units which had less plug-flow hydraulic characteristics. The empty column, which acts somewhat as an upflow clarifier, did as well as any other unit tested.

The empty column, which is a wall effect control, exhibits a fluctuating level of performance. In some cases, it functions as well as any other unit. In other cases, particularly where the feed stream varies somewhat with time, the unit functions poorly, due to "bulking," a condition in which the solids accumulated in the bottom of the unit rise, due to the accumulation of gas bubbles at their surfaces. This is a general characteristic of upflow clarifiers. In upflow sedimentation basins, it has been noted that the sludge "blanket" of solids layer rises periodically, due to upsets in the flow regime or to periods of low flow, when liquid flow is fast enough to displace the bubbles adhering to the surface. Since this is a very slow flow sedimentation basin, this is probably what occurs during the periodic upsets in the empty column.

Table VI

| Volatile Suspended Solids Removal Efficiencies | |
|---|---|
| Unit | Removal Efficiency, % |
| A | 93.5 |
| B | 89.2 |
| C | 81.8 |
| D | 73.6 |
| E | 93.5 |

Table VII

| | $BOD_5$ Removal Efficiency | | | | |
|---|---|---|---|---|---|
| | Removal Efficiency in Column | | | | |
| Bed Depth, ft. | A | B | C | D | E |
| 1 | 80.4 | 54.6 | 83.7 | 83.7 | 92.7 |
| 2 | 90.5 | 100.0 | 98.3 | 87.7 | 88.2 |
| 3 | 93.9 | 77.6 | 99.4 | 88.8 | 92.2 |
| 4 | 95.0 | 82.1 | 96.1 | 88.8 | 92.2 |
| 5 | 97.2 | 96.1 | 88.8 | 87.1 | 89.9 |
| 6 | 100.0 | 97.2 | 90.5 | 91.6 | 91.2 |

Following this, the five units were placed on a lower flow rate of 60 ml per minute per column. Another traverse of the units, similar to the data presented in Table IV was performed. This data is shown in Table VII. It was interesting to note that all of the units tested had $BOD_5$ removal efficiencies better than 90 percent. All of the units except column A clustered just above 90 percent. Column A provided a removal efficiency of almost 100%, according to the data taken. As in earlier traverses, removal efficiency did not decrease exponentially. This is probably due to the complexity and sequential nature of the degradation reactions which are taking place in the units.

Two different types of suspended solids were measured. Volatile solids were determined to provide a measure of the suspended organic matter in the system. Total suspended solids were also determined to provide a measure of the suspended solid matter in the sewage treated. The figures given in Tables VIII and IX are from sequential sampling runs separated by 24 to 48 hours. The samples were taken from the feed stream and from the effluents in the usual manner. Each sample was a 24 hour continuous sample. This was done to even out differences in the feed across a 24 hour period.

Observing the sample data in the order in which it was taken, it can be noted that the suspended solids passed out of the column across a period of several days following the exceptionally high suspended solids levels caused by digester sludge return during the period of runs 1 and 4. This caused a decrease in the apparent efficiency of solids removal during runs 2 and 5. During this period, the total suspended solids in the feed ran above 2 grams per liter on a dry weight basis, a factor of 20 to 50 above normal operation.

Table VIII

Suspended Solids Removal Efficiency

| Column | Efficiency % Run | | | | |
|---|---|---|---|---|---|
| | 1 | 2 | 3 | 4 | 5 |
| A | 98.7 | 43.9 | 97.8 | 99.6 | 90.4 |
| B | 97.0 | 56.1 | 73.4 | 99.3 | 100.0 |
| C | 94.9 | 34.2 | 88.8 | 99.3 | 75.0 |
| D | 94.1 | 13.5 | 87.9 | 97.9 | 67.3 |
| E | 99.1 | 22.6 | 94.4 | 99.9 | (1100)* |

* Upflow clarifiers were unstable. This unit was putting out 11 times its influent concentration in suspended solids.

Table IX

Volatile Suspended Solids Removal Efficiency

| Column | Efficiency % Run | | | | |
|---|---|---|---|---|---|
| | 1 | 2 | 3 | 4 | 5 |
| A | 96.6 | 48.1 | 83.1 | 97.0 | 61.5 |
| B | 94.0 | 52.0 | 73.5 | 96.4 | 71.2 |
| C | 90.5 | 25.0 | 66.2 | 97.3 | 72.9 |
| D | 90.1 | 55.8 | 79.9 | 97.7 | 67.8 |
| E | 95.6 | 55.8 | 79.9 | 97.7 | (532)* |

*Upflow clarifiers were unstable. This unit was putting out 5 ¼ times its influent concentration in volatile suspended solids.

The fermentation of two different wastes, one an industrial waste containing 1,000 ppm fermentable organic carbon, and the other a domestic waste containing 100 ppm fermentable organic carbon, processed with 80% efficiency, forms a gas containing 70% methane and 30% carbon dioxide by volume. The industrial waste produces 47 millimoles of methane, and the domestic waste, 4.7. Methane is a soluble gas. At ambient temperatures, methane is soluble in water at around 33.5 ml/l or 1.5 millimoles per liter in equilibrium with a 70% methane, 30% carbon dioxide atmosphere. Thus, the industrial waste appears to produce 45½ millimoles of methane per 1,000 ppm carbon, and the domestic waste, 32 millimoles. The methane can be removed from the effluent prior to discharge. However, assuming that the rate of carbon fermentation per unit volume of process equipment is the same, dilute wastes appear to produce less methane than do more concentrated waste streams for each unit of process volume.

The sewage in this experiment was generally 40 to 100 ppm organic carbon. Assuming, based on the $BOD_5$ removal, a conversion of 85% of the waste to gas, and a yield of 70% methane in the gas, 4 liters of methane per pilot unit per day at a flow rate of 60 ml per unit per minute should be produced. The data generally show 2 to 4 liters of gas per unit per day.

The anaerobic unit of this invention produces more methane per volume of waste processed than a conventional aerobic system. The conventional aerobic system converts about one-half to three-fourths of the carbon in the system to carbon dioxide. The sludge, or waste microorganisms and waste non-degradable materials are processed in a digestor for a period of around twenty days. During this period, about half of the residual carbon is converted to gas containing 70% methane. Thus, about 1 millimole of methane for every liter of 100 ppm carbon domestic sewage which is processed is produced.

EXAMPLE IV

A membrane disruptive detergent has been used for the removal of microorganisms which have ceased to respire from a culture of respiring and non-respiring microorganisms. The concentrations of detergent required to lyse small percentages of the population are less than about 15 ppm. This is within the amounts of detergent which can be reasonably afforded in the course of treatment of an industrial waste. To prevent the build-up of dead biomass within a column unit, an experiment using the following feed to a nitrate reducing four column unit containing denitrifying microorganisms was used:

| | |
|---|---|
| Ethylene glycol | 7900 ppm |
| Yeast Extract | 57 ppm |
| Sodium nitrate | 11500 ppm |
| Dibasic sodium phosphate | 100 ppm |
| Phosphoric acid | 25 ppm |
| Triton X 100 detergent (a non-ionic surfactant composed of an aryl alkyl polyether alcohol) | 3 ppm |

The units were operated successfully over a period of about a year without clogging. During the course of a day, the units were fed with 26 gallons of this feed. The units are 7.5 inch ID × 6 feet high and hold about 1.8 cubic feet. The waste treatment removes over 98% of the influent nitrate under most circumstances. The detergent also provides foam control.

It is thus seen that by the process of this invention a new process for conducting anaerobically catalyzed reactions involving a limited microbe population has been developed. Many variations of this disclosed process will be made apparent to those of skill in the art from a reading of the above description. However, such variations are embodied within the scope of the appended claims.

What is claimed is:

1. A process for carrying out a biologically catalyzed reaction comprising the steps of:
    introducing an influent solution containing reactants into the lower section of an upflow packed bed column packed with a support material for microorganisms, said support material having attached thereto anaerobic microorganisms for catalyzing the reaction of said reactants;
    introducing with said influent a membrane disruptive detergent to lyse dead microorganisms from said support and to make available the essential nutrient of said dead microorganisms to the remaining live microoganisms;
    allowing said reactants to react under the influence of said anaerobic microorganisms; and
    simultaneously with said steps of introducing and allowing restricting the presence of an essential growth nutrient within said influent solution to cause the population of said anaerobic microorganism to remain substantially constant and to prevent said anaerobic microorganisms from plugging said packed column.

2. The process according to claim 1 wherein said microorganisms convert BOD of said influent solution to methane.

3. The process according to claim 1 wherein said influent contains glucose as a reactant wherein said glucose is converted to ethanol by said microorganisms and wherein said microoganisms are yeast and the presence of nitrogen is restricted to cause the population of said microorganisms to remain substantially constant.

4. The process according to claim 1 wherein said support material has a hydrophilic charged surface having anaerobic microorganisms attached to said hydrophilic charged surface.

5. The process according to claim 1 wherein said support material has a polymeric surface having anaerobic microorganisms attached to said polymeric surface.

6. The process according to claim 1 wherein said support material has a crosslinked polymeric surface having anaerobic microorganisms attached to said crosslinked polymeric surface.

7. The process according to claim 6 wherein said influent contains glucose as a reactant wherein said glucose is converted to ethanol by said microorganisms and wherein said microorganisms are yeast and the presence of nitrogen is restricted to cause the population of said microorganisms to remain substantially constant.

8. A process for carrying out a biologically catalyzed reaction comprising the steps of:
introducing an influent solution containing reactants into the lower section of an upflow packed bed column packed with a support material for microorganisms, said support material having attached thereto anaerobic microorganisms for catalyzing the reaction of said reactants, said column containing predatory protozoa which consume anaerobic microorganisms and excrete essential nutrients consumed from said consumed anaerobic microorganisms for use by the remaining live anaerobic microorganisms;
allowing said reactants to react under the influence of said anaerobic microorganisms; and
simultaneously with said steps of introducing and allowing, restricting the presence of an essential growth nutrient within said influent solution to cause the population of said anaerobic microorganism to remain substantially constant and to prevent said anaerobic microorganisms from plugging said packed column.

9. The process according to claim 8 wherein said protozoa are identified as ATCC Culture No. 30539.

10. The process according to claim 8 wherein said support material has a hydrophilic charged surface having microorganisms attached to said hydrophilic charged surface.

11. The process according to claim 8 wherein said support material has a polymeric surface having anaerobic microorganisms attached to said polymeric surface.

12. The process according to claim 8 wherein said support material has a crosslinked polymeric surface having anaerobic microorganisms attached to said crosslinked polymeric surface.

13. The process according to claim 11 in which said influent solution comprises waste containing fermentable organic carbon, and said support material having attached microorganisms is prepared by the method comprising the steps of:
forming a mixture of rumen fluid, sewage sludge, and a polyelectrolyte;
contacting a support material with said mixture to cause organisms present in said mixture to attach to said support material; and
incubating microorganisms on said support in an environment comprising waste containing fermentable organic carbon.

14. The process according to claim 13 in which said waste comprises municipal sewage.

* * * * *